(12) United States Patent
Shieh et al.

(10) Patent No.: US 6,670,477 B2
(45) Date of Patent: Dec. 30, 2003

(54) SYNTHESIS OF ENANTIOMERICALLY ENRICHED 4-PIPERIDINYLGLYCINE

(75) Inventors: Wen-Chung Shieh, Berkeley Heights, NJ (US); Song Xue, Parsippany, NJ (US); Noela Marjory Reel, Ho-Ho-Kus, NJ (US); John Joseph Fitt, Denville, NJ (US)

(73) Assignee: Novartis AG, Basel (CH)

( * ) Notice: Subject to any disclaimer, the term of this patent is extended or adjusted under 35 U.S.C. 154(b) by 53 days.

(21) Appl. No.: 10/090,087

(22) Filed: Mar. 4, 2002

(65) Prior Publication Data

US 2002/0133014 A1 Sep. 19, 2002

Related U.S. Application Data

(60) Provisional application No. 60/275,811, filed on Mar. 14, 2001.

(51) Int. Cl.⁷ ............... C07D 211/22; C07D 211/26; C07D 211/32
(52) U.S. Cl. ............ 546/220; 546/246; 546/248
(58) Field of Search ............... 546/220, 11, 246, 546/248

(56) References Cited

U.S. PATENT DOCUMENTS 5,817,822 A    10/1998   Nantermet et al. ......... 546/194

FOREIGN PATENT DOCUMENTS

WO          2002072577    *   9/2002

OTHER PUBLICATIONS

Adamczyk et al., "An Efficient Enantioselective Synthesis of (S)–(–)–Acromelobic Acid", Org. Lett., vol. 2, No. 22, pp. 3421–3423 (2000).

Jones et al., "Preparation of (S)–2–Quinolylalanine by Asymmetric Hydrogenation", Tetrahedron Letts., vol. 40, pp. 1211–1214 (1999).

Burk et al., "Asymmetric Catalytic Synthesis of β–Branched Amino Acids via Highly Enantioselctive Hydrogenation Reactions", J. Am. Chem. Soc., vol. 117, p. 9375, Suppl. pp. 1–18 (1995).

Shieh et al., "An Enantioselective Synthesis of (R)–4–Piperidinylglycine", Tetrahedron: Asymmetry, vol. 12, pp. 2421–2425 (2001).

* cited by examiner

*Primary Examiner*—Rita Desai
(74) *Attorney, Agent, or Firm*—Paivi J. Kukkola; John D. Thallemer

(57) ABSTRACT

A process for making enantiomerically enriched 4-piperidinylglycine having the formula (I),

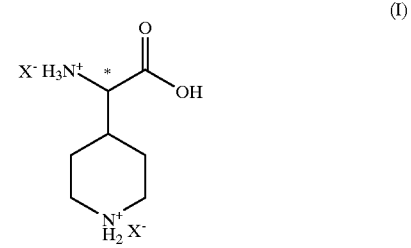

said process comprising (a) combining N-protected glycine ester with 4-piperidone to form didehydroamino acid ester; (b) reducing the didehydroamino acid ester with hydrogen gas in the presence of a rhodium catalyst selected from the group consisting of (R,R)-BPE-Rh; (S,S)-BPE-Rh; (R,R)-DuPHOS-Rh; (S,S)-DuPHOS-Rh; and combinations thereof; whereby a protected compound is formed; and (c) removing the protecting groups from the protected compound, whereby the 4-piperidinylglyeine having the formula (I) is formed, wherein $X^-$ is an anion wherein X is independently a halogen; and "*" designates an asymmetric carbon having (R)- or (S)-configuration. The process of the invention yields an enantiomerically enriched (R)-4-piperidineglycine or (S)-4-piperidineglycine.

17 Claims, No Drawings

SYNTHESIS OF ENANTIOMERICALLY ENRICHED 4-PIPERIDINYLGLYCINE

This application claims priority from U.S. Provisional Application No. 60/275,811 filed Mar. 14, 2001, the disclosure of which is herein incorporated by reference.

FIELD OF THE INVENTION

The present invention provides a process for making enantiomerically enriched 4-piperidinylglycine.

BACKGROUND OF THE INVENTION

4-Piperidinylglycine is an important amino acid which has been used in synthesizing pharmaceutical ingredients such as matrix metalloproteinase inhibitor and thrombin inhibitor. While racemic piperidinylglycine has been synthesized by hydrogenation of an enamide substrate, enantiomerically enriched piperdinylglycine is much more difficult to synthesize.

U.S. Pat. No. 5,817,822 describes an enantioselective synthesis of (R)-N-t-Boc-4-piperidinylglycine using optically active (R)-4-benzyl-2-oxazolidinone as a chiral auxiliary. (R)-N-t-Boc-4-piperidinylglycine is prepared by an 8-step synthetic sequence utilizing R-(+)-4-benzyl-2-oxazolidinone as a chiral auxiliary and trisyl azide as an electrophile. This method works well for the preparation of small quantities of 4-piperidinylglycine for drug discovery activities, however, for scale up synthesis, this method is economically unsatisfactory due to the many steps involved, and potentially unsafe due to the handling of 2,4,6-triisopropylbenzenesulfonyl azide (trisyl azide), which is thermally unstable.

Chiral rhodium catalysts have been used in asymmetric synthesis of heterocyclic amino acids as described by Burk, M. J.; Gross, M. F.; Martinez, J. P. in *J. Am. Chem. Soc.*, 117, 9375–9376 (1995); Adamczyk, M.; Akireddy, S. R.; Reddy, R. E. in *Organic Letters*, 2, 3421–3423 (2000); Tiffin, P. D.; Jones, S. W.; Palmer, C. F.; Paul, J. M. in *Tetra. Lett.*, 40, 1211–1214 (1999).

Therefore, it is desirable to develop a more direct synthesis for 4-piperidinylglycine which does not involve using 2,4,6-triisopropylbenzenesulfonyl azide.

SUMMARY OF THE INVENTION

The invention provides a process for making enantiomerically enriched 4-piperidinylglycine having the formula (I)

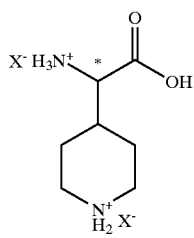

(I)

said process comprising
(a) combining N-protected glycine ester having the formula (II)

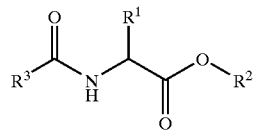

(II)

with 4-piperidone having the formula (III)

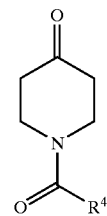

(III)

whereby didehydroamino acid ester is formed having the formula (IV);

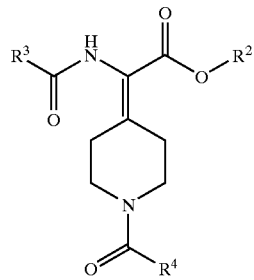

(IV)

(b) reducing the didehydroamino acid ester (IV) with hydrogen gas in the presence of a catalyst selected from the group consisting of (R,R)-BPE-Rh having the formula (A1), (S,S)-BPE-Rh having the formula (A2), (R,R)-Me-DuPHOS-Rh having the formula (B1), (S,S)-Me-DuPHOS-Rh having the formula (B2), and combinations thereof;

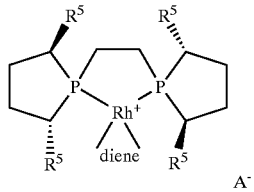

(A1)

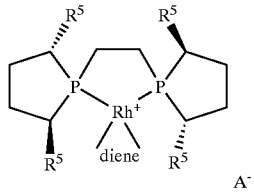

(A2)

-continued

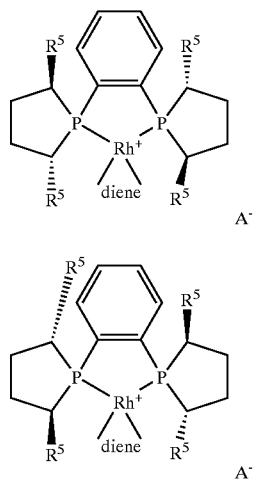

(B1)

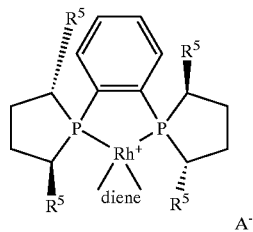

(B2)

whereby a protected chiral compound is formed having the formula (V);

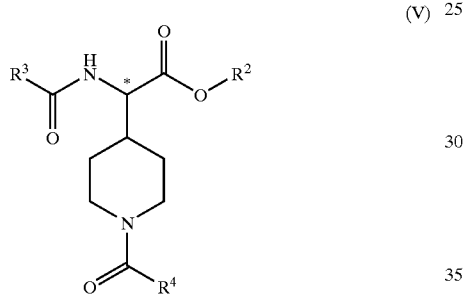

(V)

(c) removing the protecting groups of formula (V), whereby the 4-piperidinylglycine having the formula (I) is formed; wherein $R^1$ is selected from the group consisting of hydrogen and $PO(OM)_2$, wherein M is a phenyl or $C_1$–$C_8$ linear, branched or cyclic alkyl group; $R^2$ is selected from the group consisting of hydrogen, phenyl and a $C_1$–$C_8$ linear, branched or cyclic alkyl group; $R^3$ and $R^4$ are independently selected from the group consisting of hydrogen, phenyl, a $C_1$–$C_8$ linear, branched or cyclic alkyl group, and $OR^6$, wherein $R^6$ is selected from the group consisting of hydrogen, phenyl, benzyl, substituted benzyl, and $C_1$–$C_8$ linear, branched or cyclic alkyl group; $R^5$ is independently selected from the group consisting of a $C_1$–$C_8$ linear, branched or cyclic alkyl group, a $C_1$–$C_8$ linear, branched or cyclic fluoroalkyl group, and combinations thereof; diene is a counter ligand independently selected from the group consisting of cyclooctadiene (COD) and norbornadiene (NBD); $A^-$ is an anion wherein A is independently selected from the group consisting of trifluoromethanesulfonate (OTf), tetrafluoroborate ($BF_4$), hexafluoroantimonate ($SbF_6$) and hexafluorophosphate ($PF_6$); $X^-$ is an anion wherein X is independently a halogen; and "*" designates an asymmetric carbon having (R)- or (S)- configuration.

The process of the invention yields an enantiomerically enriched 4-piperidineglycine in excellent yield. As used herein, "enantiomerically enriched" 4-piperidinylglycine means at least 60% enantiomeric excess, preferably at least 80% entantiomeric excess, most preferably at least 98% enantiomeric excess, of 4-piperidinylglycine.

DESCRIPTION OF THE INVENTION

The process of the invention is used to prepare 4-piperidinylglycine having the formula (I)

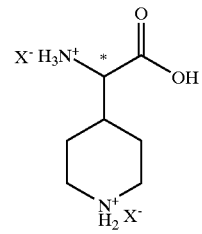

(I)

wherein $X^-$ is an anion wherein X is independently a halogen; and "*" designates an asymmetric carbon having (R)- or (S)-configuration. Preferably the halogen is chlorine. The process involves at least three steps. In the first step, Step (a), N-protected glycine ester having the formula (II)

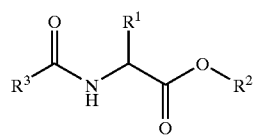

(II)

is combined with 4-piperidone having the formula (III)

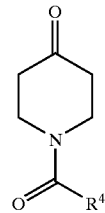

(III)

to form didehydroamino acid ester having the formula (IV);

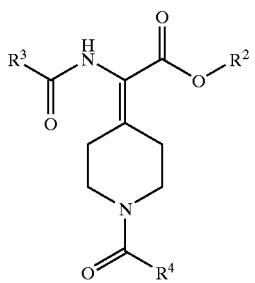

(IV)

wherein $R^1$ is selected from the group consisting of hydrogen and $PO(OM)_2$, wherein M is a phenyl or $C_1$–$C_8$ linear, branched or cyclic alkyl group. Preferably, $R^1$ is $PO(OCH_3)_2$. $R^2$ is selected from the group consisting of hydrogen, phenyl and a $C_1$–$C_8$ linear, branched or cyclic alkyl group. Preferably $R^2$ is methyl. $R^3$ and $R^4$ are independently selected from the group consisting of hydrogen, phenyl, a $C_1$–$C_8$ linear, branched or cyclic alkyl group, and $OR^6$, wherein $R^6$ is selected from the group consisting of hydrogen, phenyl, benzyl, substituted benzyl, and $C_1$–$C_8$ linear, branched or cyclic alkyl group. Preferably, $R^3$ is $OCH_2Ph$. Preferably, $R^4$ is $OC(CH_3)_3$. $X^-$ is an anion wherein X is independently a halogen; and "*" designates an asymmetric carbon having (R)- or (S)-configuration.

In the second step, Step (b), the didehydroamino acid ester (IV) is reduced with hydrogen gas. The reduction takes place in the presence of a rhodium catalyst. The selection of rhodium catalyst is critical to the enantioselective process of the invention. The rhodium catalyst may be present as (R,R) or (S,S) which is used to prepare either the enantiomerically enriched (R)-4-piperdinylglycine or (S)-4-piperdinylglycine, respectively. The rhodium catalyst is selected from the group consisting of (R,R)-BPE-Rh having the formula (A1), (S,S)-BPE-Rh having the formula (A2), (R,R)-DuPHOS-Rh having the formula (B 1), (S,S)-DuPHOS-Rh having the formula (B2), wherein $R^5$ is independently selected from the group consisting of a $C_1$–$C_8$ linear, branched or cyclic alkyl group, a $C_1$–$C_8$ linear, branched or cyclic fluoroalkyl group, and combinations thereof, diene is a counter ligand independently selected from the group consisting of cyclooctadiene (COD) and norbornadiene (NBD). $A^-$ is an anion wherein A is independently selected from the group consisting of trifluoromethanesulfonate (OTf), tetrafluoroborate ($BF_4$), hexafluoroantimonate ($SbF_6$) and hexafluorophosphate ($PF_6$). The rhodium catalysts' [(Me-BPE)-Rh-(COD)]OTf and [(Me-DuPHOS)-Rh-(COD)]OTf are commercially available from Strem Chemicals Inc. A combination of catalysts may also be used.

(A1)

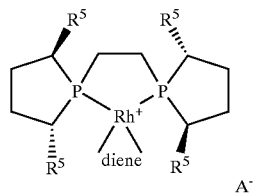

(A2)

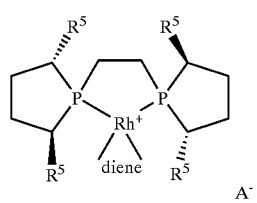

(B1)

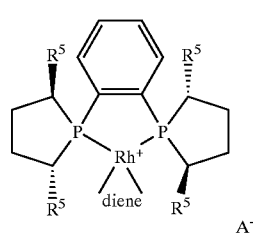

(B2)

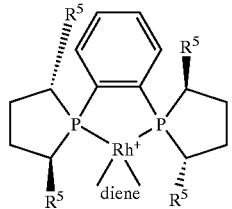

Preferably, the rhodium catalyst is selected from [((R,R)-Me-BPE-Rh-(COD)]OTf, [((S,S)-Me-BPE-Rh-(COD)]OTf, [((R,R)-Me-DuPHOS-Rh-(COD)]OTf, or [((S,S)-Me-DuPHOS-Rh-(COD)]OTf having the respective formulas T1, T2, T3, T4, (T1)

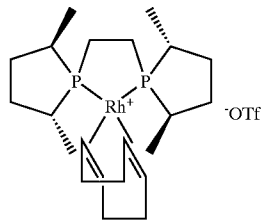

(T2)

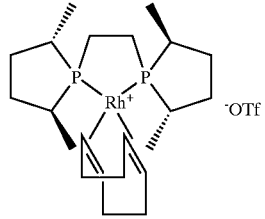

(T3)

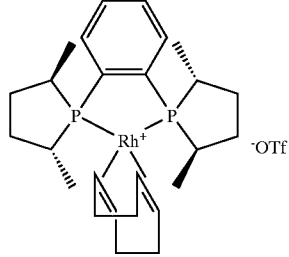

(T4)

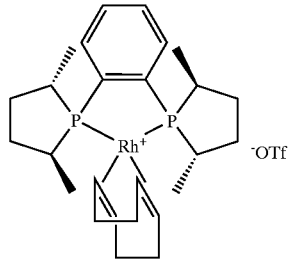

The reduction in Step (b) is preferably conducted at a temperature of from about 0° C. to about 60°, more preferably, 20° C. to 28° C.; and under gaseous hydrogen pressure of from about 1 atm to about 200 atm, more preferably, 50 atm to 100 atm.

The reduction in Step (b) results in the formation of a protected compound having the formula (V) which contains an asymmetric carbon as designated by a "*" sign,

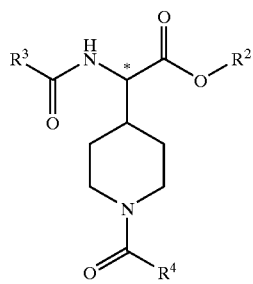

(V)

In the compound of formula (V), $R^2$ is selected from the group consisting of hydrogen, phenyl and a $C_1$–$C_8$ linear, branched or cyclic alkyl group. Preferably $R^2$ is methyl. $R^3$ and $R^4$ are independently selected from the group consisting of hydrogen, phenyl, a $C_1$–$C_8$ linear, branched or cyclic alkyl group, and $OR^6$, wherein $R^6$ is selected from the group consisting of hydrogen, phenyl, benzyl, substituted benzyl, and $C_1$–$C_8$ linear, branched or cyclic alkyl group. Preferably, $R^3$ is $OCH_2Ph$. Preferably, $R^4$ is $OC(CH_3)_3$.

In the third step, Step (c), at least one protecting group is removed from the protected compound formed in Step (b). In one embodiment of the invention, all three protecting groups are removed in one step from the compound of formula (V) to form the 4-piperidinylglycine having the formula (I).

In another embodiment of the invention, two protecting groups are removed from the compound of formula (V), whereby a semi-protected compound is formed having the formula (VII)

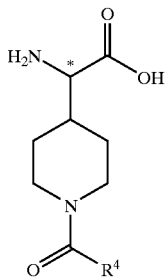

(VII)

wherein $R^4$ is selected from the group consisting of hydrogen, phenyl, a $C_1$–$C_8$ linear, branched or cyclic alkyl group, and $OR^6$, wherein $R^6$ is selected from the group consisting of hydrogen, phenyl, benzyl, substituted benzyl, and $C_1$–$C_8$ linear, branched or cyclic alkyl group. Preferably, $R^4$ is $OC(CH_3)_3$. In an optional fourth step, Step (d), the protecting group in formula (VII) is removed to form the 4-piperidinylglycine having the formula (I).

Following removal of at least one protecting group, the desired enantiomeric 4-piperidinylglycine may optionally be separated by physical or chemical means to increase the enantiomeric excess. Examples of such means for separation include, but are not limited to, crystallization, chemical resolution, and chiral preparative chromatography such as high pressure liquid chromatography (HPLC). An especially preferred means for increasing the enantiomeric excess is crystallization of the semi-protected 4-piperidinylglycine of formula (VII).

The above-mentioned steps are carried out according to standard methods, in the presence or absence of diluent, preferably such as are inert to the reagents and are solvents thereof, condensing or said other agents respectively and/or inert atmospheres, at low temperatures, room temperature or elevated temperatures, and at atmospheric or super-atmospheric pressure.

The compounds of the invention exhibit valuable pharmacological properties in mammals including man, particularly as inhibitors of TNF-α-activity and as inhibitors of matrix-degrading metalloproteinase enzymes.

The following nonlimiting examples illustrate further aspects of the invention.

EXAMPLE 1

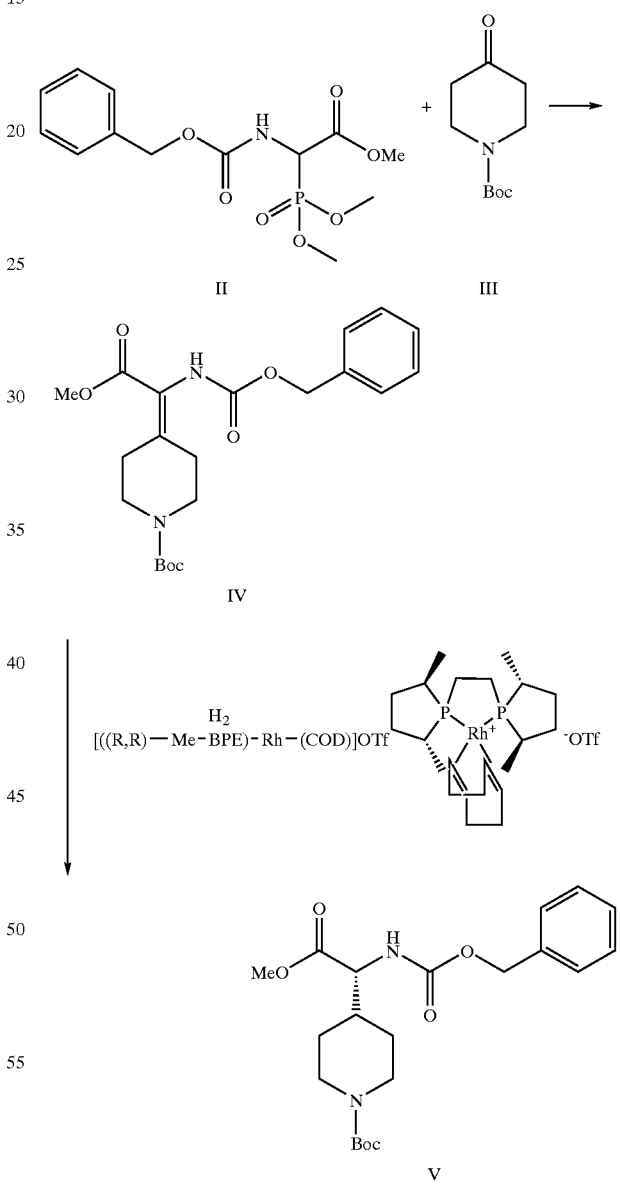

In the first step, N-(α)-Cbz-phosphonoglycine trimethyl ester having formula (II) was reacted with N-Boc-4-piperidone having formula (III) to form 4-(benzyloxycarbonylamino-methoxycarbonyl-methylene)-piperidine-1-carboxylic acid tert-butyl ester having formula (IV) as follows:

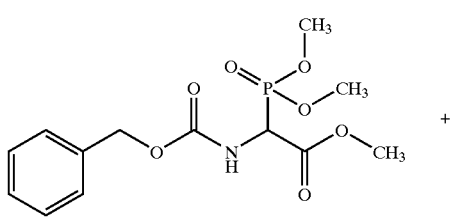

II

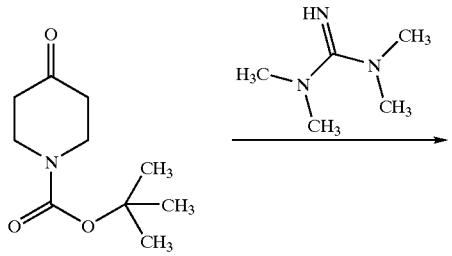

III

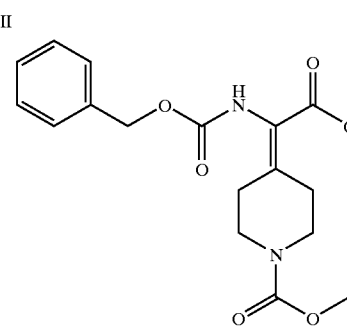

IV

A 250-mL, three necked, round-bottomed flask equipped with mechanical stirrer and 50 mL pressure equalizing addition funnel was charged with N-Cbz-phosphonoglycine trimethyl ester (9.94 g, 0.030 mol) and tetrahydrofuran (20 mL) under nitrogen purge. Tetramethylguanidine (4.50 g, 0.039 mol) was added and the solution was stirred for 15 min. A solution of N-Boc-4-piperidone (16.74 g, 0.084 mol) in tetrahydrofuran (30 mL) was added via addition funnel over 5 min. The solution was stirred at ambient temperature for 21 hours. Tetrahydrofuran was removed via rotary evaporator and ethyl acetate (100 mL) was added. The organic solution was washed with 5% aqueous citric acid solution (150 mL), saturated sodium bicarbonate solution (50 mL) saturated sodium chloride solution (50 mL), dried over magnesium sulfate, and evaporated to give an oil, which was dissolved in ethyl acetate (12 mL). Hexane (60 mL) was added to precipitate the product. The crude product was filtered and recrystallized from ethyl acetate:hexane (1:4 ratio) to yield 6.91 g (57%) of 4-(benzyloxycarbonylamino-methoxycarbonyl-methylene)-piperidine-1-carboxylic acid tert-butyl ester as a white solid.

The 4-(benzyloxycarbonylamino-methoxycarbonyl-methylene)-piperidine-1-carboxylic acid tert-butyl ester was analyzed using Proton magnetic resonance spectra recorded on an FT-NMR spectrometer either on Brüker ARX300 or DRX500, and Chiral HPLC performed on a Waters HPLC system with a 996 PDA detector. The following data was obtained: mp 101.5–102.6° C.; IR (KBr) 3312, 2972, 1725, 1703, 1684, 1512, 1477, 1451, 1426, 1365, 1327, cm$^{-1}$; $^1$H NMR (500 MHz, CDCl$_3$) δ 7.49–6.30 (m, 5H), 6.17 (br s, 1H), 5.13 (s, 2H), 3.76–3.68(m, 3H), 3.56–3.40 (m, 4H), 2.92–2.78 (m, 2H), 2.39 (t, J=5.9 Hz, 2H), 1.47 (s, 9H); $^{13}$C NMR (125 MHz, CDCl$_3$) δ 165.4, 155.1, 147.6, 136.4, 128.9, 128.8, 128.7, 128.6, 120.6, 80.2, 67.8, 53.3, 44.2, 43.43, 30.8, 30.1, 28.9, 28.8. Analysis calculated for $C_{21}H_{28}N_2O_6$: C, 62.36; H, 6.98; N, 6.93. Found: C, 62.43; H, 7.07; N, 6.83.

In the second step, 4-(benzyloxycarbonylamino-methoxycarbonyl-methylene)-piperidine-1-carboxylic acid tert-butyl ester having formula (IV) is asymmetric hydrogenated to form a protected piperdinylglycine having formula (V).

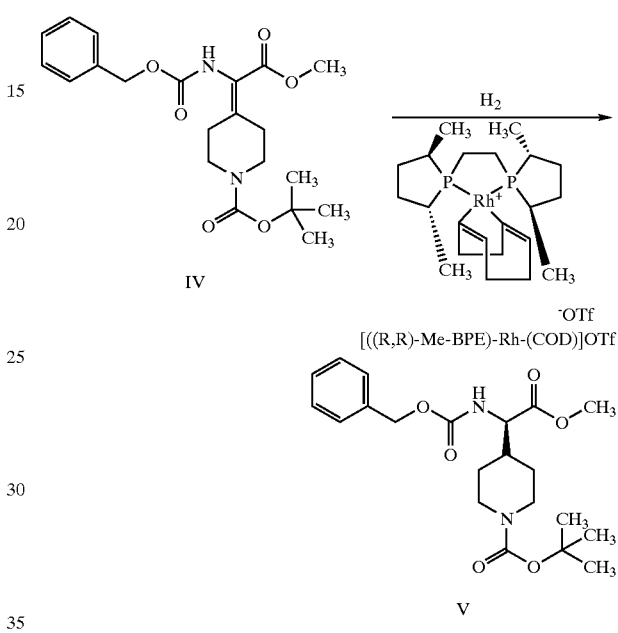

A Parr bottle was charged with 4-(benzyloxycarbonylamino-methoxycarbonyl-methylene)-piperidine-1-carboxylic acid tert-butyl ester (0.37 g, 0.9 mmol) and degassed MeOH (40 mL) under nitrogen purge. To this colorless solution, [((R,R)-Me-BPE)-Rh-(COD)]OTf catalyst (10 mg) was quickly added. The resulting solution was vacuumed and refilled with nitrogen for three cycles, and then vacuumed and refilled with hydrogen for an additional three cycles. The solution was stirred under 90 psi of hydrogen gas at room temperature over 24 hours. The mixture was concentrated on a rotary evaporator to remove MeOH. The residue was redissolved into ethyl acetate (20 mL) and filtered through a silicon pad (3 g) to remove the catalyst. The silicon cake was rinsed with ethyl acetate (20 mL). The combined filtrate was concentrated to afford 0.37 g (100% yield) of a compound having formula (V) as an oil.

The compound having formula (V) was analyzed using Proton magnetic resonance spectra recorded on an FT-NMR spectrometer either on Brüker ARX300 or DRX500, and Chiral HPLC performed on a Waters HPLC system with a 996 PDA detector. The following data was obtained: Rf=0.36 (Hexane/EtOAc 1/1); [α]$^{25}_D$ –20.7 (c=1.05, CHCl$_3$); chiral HPLC 94% e.e.: (+)-enantiomer, 3%, Rt 7.21 min, (–)-enantiomer, 97%, Rt 10.04 min, (Chiralcel OD column, Hexane/IPA/TFA 9/1/0.1%, flow rate 1.5 mL/min); IR (KBr) 3323, 2950, 1691, 1529 cm$^{-1}$; $^1$H NMR (300 MHz, CDCl$_3$)7.32–7.42 (m, 5H), 5.32 (d, J=8.7 Hz, 1H), 5.12 (s, 2H), 4.33–4.44 (m, 1H), 4.08–4.21 (m, 2H), 3.77 (s, 3H), 2.57–2.76 (m, 2H), 1.85–2.02 (m, 1H), 1.40–1.70 (m, 2H), 1.46 (s, 9H), 1.19–1.39 (m, 2H); $^{13}$C NMR (125 MHz, CDCl$_3$) 171.8, 156.0, 154.6, 136.0, 128.5, 128.2, 128.1, 79.5, 67.1, 57.8, 52.3, 43.4, 39.6, 28.3, 27.1. Analysis calculated for $C_{21}H_{30}O_6N_2$: C, 62.05; H, 7.44; N, 6.89. Found: C, 61.99; H, 7.09; N, 7.04.

In the third step, protected piperdinylglycine is converted to a carboxylic acid having formula (VI).

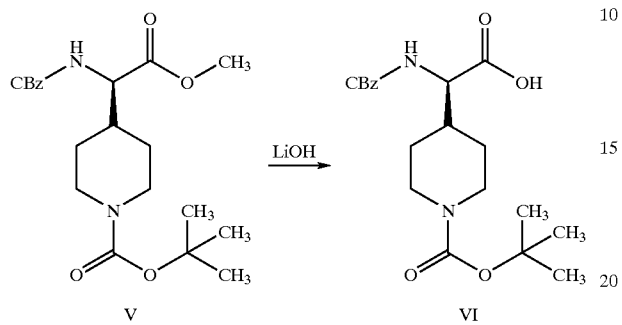

A 250 mL flask equipped with a magnetic stirrer was charged with (V) (2.8 g, 6.9 mmol) and MeOH (103 mL). The solution was cooled to 5° C. with an ice bath. A solution of 1 N LiOH (35 mL, 35 mmol, made from 1.5 g of LiOH.H₂O in 33.5 mL of H₂O) was added and the mixture was allowed to warm up to room temperature and stirred for another 20 h. The reaction mixture was neutralized with 1 N KHSO₄ solution and concentrated in vacuo to remove MeOH. Ethyl acetate (50 ml) was added to the mixture. The pH of the aqueous layer was adjusted to 2 with 2 N KHSO₄ and the organic layer was separated. The aqueous layer was further extracted with ethyl acetate (2×50 mL). The combined ethyl acetate layers were washed with 50 mL of brine, dried over MgSO₄, filtered through celite, and concentrated under vacuum to give 2.6 g (97% yield) of a compound having formula (VI) as white foamy solid.

The compound of formula (VI) was analyzed using Proton magnetic resonance spectra recorded on an FT-NMR spectrometer either on Brüker ARX300 or DRX500, and Chiral HPLC performed on a Waters HPLC system with a 996 PDA detector. The following data was obtained: $[\alpha]^{25}_D$–18.6 (c=1.07, CHCl₃); chiral HPLC 90% e.e.: (+)-enantiomer, 5%, Rt 5.72 min, (–)-enantiomer, 95%, Rt 8.54 min, (Chiralcel OD, Hexane/IPA/TFA 9/1/0.1%, flow rate 1.5 mL/min). IR (KBr) 3327, 2977, 2931, 1695, 1531, 1479, 1367, 1243, 1164 cm⁻¹; ¹H NMR (500 MHz, CDCl₃) δ 8.30–9.20(bs, 1H), 7.30–7.40(m, 5H), 5.49(d, J=8.7 Hz, 1H), 5.13(s, 2H), 4.34–4.50 (m, 1H), 4.03–4.30(m, 2H), 2.57–2.80(m, 2H), 1.95–2.09(m, 1H), 1.46 (s, 9H), 1.22–1.78(m, 4H); ¹³C NMR (125 MHz, CDCl₃) δ 175.1, 156.7, 155.4, 136.4, 129.0, 128.7, 128.5, 80.5, 67.7, 58.1, 44.0, 39.7, 28.8, 27.3; Analysis calculated for $C_{20}H_{28}O_6N_2$: C, 61.21; H, 7.19; N, 7.14. Found: C, 60.98; H, 6.93; N, 7.14.

In the fourth step, the compound of formula (VI) was converted to a compound having formula (VII).

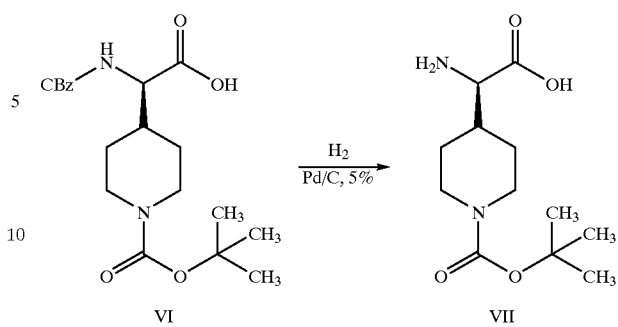

A Parr bottle was charged with 5% Pd/C (0.27 g) under nitrogen atmosphere. A solution of the compound having formula (VI) (1.25 g, 3.2 mmol) in MeOH (14 mL) and H₂O (8 mL) were added under nitrogen purge. The mixture was vacuumed and refilled with nitrogen three times, then vacuumed and refilled with hydrogen for another three times. The mixture was hydrogenated under 52-psi hydrogen gas at room temperature for 3 hours. The mixture was filtered and the catalyst cake was rinsed with EtOH (100 mL). The filtrate was concentrated under vacuum to azeotropically remove H₂O. The gray solid residue was suspended in MeOH (20 mL), stirred at 60° C. for 2 hours, cooled to 0° C., and stirred for an additional 1 hour. The mixture was filtered and the solid cake was rinsed with cold MeOH (10 mL). The solid was dried under vacuum to obtain 0.7 g (85% yield) of the compound of formula (VII) as gray solid.

The compound having formula (VII) was analyzed using Proton Magnetic Resonance Spectra recorded on an FT-NMR spectrometer either on Brüker ARX300 or DRX500, and Chiral HPLC performed on a Waters HPLC system with a 996 PDA detector. The following data was obtained: $[\alpha]^{25}_D$–4.2 (c=0.51, H₂O); chiral HPLC 98% e.e.: (–)-enantiomer, 99%, Rt 13.98 min, (+)-enantiomer, 1%, Rt 23.37 min, (Crownpak CR+, perchloric acid pH 1.5/MeOH 85/15, flow rate 1 mL/min). ¹H NMR (500 MHz, D₂O) δ 4.18 (m, 2H), 3.68 (d, J=4.9 Hz, 1H), 2.76–2.92 (m, 2H), 2.09–2.21 (m, 1H), 1.74–1.83 (m, 1H), 1.64–1.72 (m, 1H), 1.48 (s, 9H), 1.25–1.53 (m, 2H); ¹³C NMR (125 MHz, CDCl₃) δ 173.2, 156.4, 81.7, 58.9, 43.6, 37.0, 27.6, 26.9. Analysis calculated for $C_{12}H_{22}O_4N_2$: C, 55.80; H, 8.58; N, 10.84. Found: C, 55.67; H, 8.35; N, 10.79.

In the fifth step, (–)-Amino-piperidin-4-yl-acetic acid dihydrochloride having formula (I) is formed.

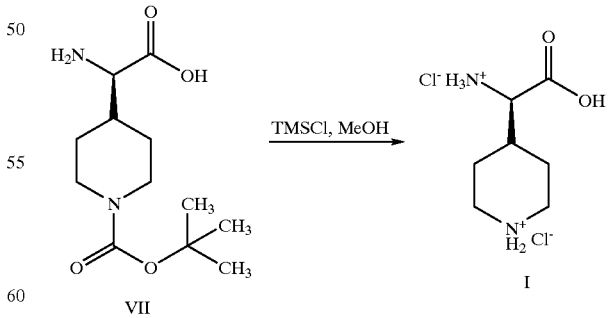

A 50 mL flask equipped with a magnetic stirrer was charged with the compound having formula (VII) (0.16 g, 0.6 mmol) and MeOH (15 mL). To the suspension, trimethylsilyl chloride (2.0 g, 18.4 mmol) was added in one portion. The solution was stirred at room temperature for 3 hours.

The reaction mixture was concentrated to obtain an oily residue. The oily residue was dried under high vacuum to give 0.11 g (79% yield) of (I) as a white foamy solid.

The compound having formula (I) was analyzed using Proton magnetic resonance spectra recorded on an FT-NMR spectrometer either on Brüker ARX300 or DRX500, and Chiral HPLC performed on a Waters HPLC system with a 996 PDA detector. The following data was obtained: $[\alpha]^{25}_D$ −18.3 (c=1.05, H$_2$O); IR (KBr) 3416, 2926, 1740, 1597, 1512, 1215 cm$^{-1}$; $^1$H NMR (300 MHz, D$_2$O) δ 3.80 (d, J=4.8 Hz, 1H), 3.33–3.48 (m, 2H), 2.84–3.01 (m, 2H), 2.10–2.29 (m, 1H), 1.81–2.01(m, 2H), 1.58–1.78(m, 1H), 1.38–1.57 (m, 1H);ES-MS 157.13 (M$^+$−1); Analysis calculated for C$_7$H$_{16}$O$_4$N$_2$Cl$_2$: C, 36.38; H, 6.98; N, 12.12. Found: C, 36.96; H, 7.38; N, 11.63.

While the invention has been described with particular reference to certain embodiments thereof, it will be understood that changes and modifications may be made by those of ordinary skill within the scope and spirit of the following claims:

What is claimed is:

1. A process for making enantiomerically enriched 4-piperidinylglycine having the formula (I),

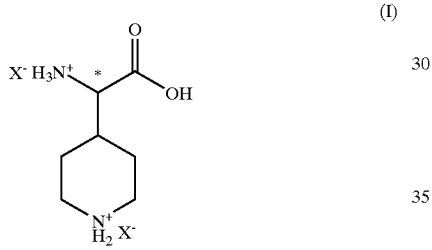
(I)

said process comprising (a) combining N-protected glycine ester having the formula (II)

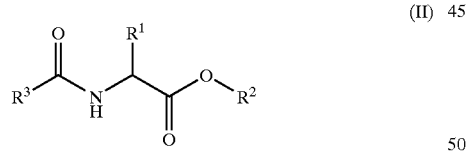
(II)

with 4-piperidone having the formula (III)

(III)

whereby didehydroamino acid ester is formed having the formula (IV);

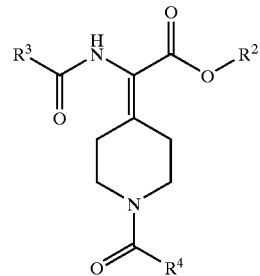
(IV)

(b) reducing the didehydroamino acid ester (IV) with hydrogen gas in the presence of a rhodium catalyst selected from the group consisting of (R,R)-BPE-Rh having the formula (A1), (S,S)-BPE-Rh having the formula (A2), (R,R)-DuPHOS-Rh having the formula (B1), (S,S)-DuPHOS-Rh having the formula (B2), and combinations thereof;

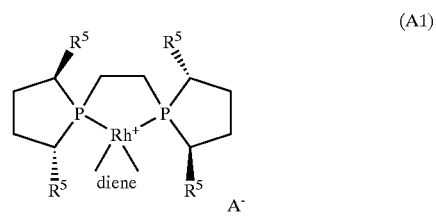
(A1)

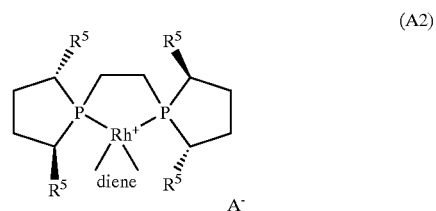
(A2)

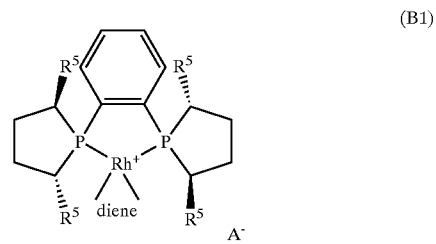
(B1)

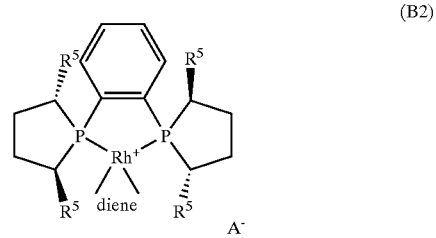
(B2)

whereby a protected compound is formed having the formula (V);

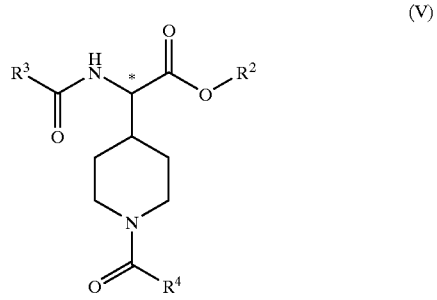

(V)

(c) removing the protecting groups of formula (V), whereby the 4-piperidinylglycine having the formula (I) is formed;

wherein $R^1$ is selected from the group consisting of hydrogen and $PO(OM)_2$, wherein M is a phenyl or $C_1$–$C_8$ linear, branched or cyclic alkyl group; $R^2$ is selected from the group consisting of hydrogen, phenyl and a $C_1$–$C_8$ linear, branched or cyclic alkyl group; $R^3$ and $R^4$ are independently selected from the group consisting of hydrogen, phenyl, a $C_1$–$C_8$ linear, branched or cyclic alkyl group, and $OR^6$, wherein $R^6$ is selected from the group consisting of hydrogen, phenyl, benzyl, substituted benzyl, and $C_1$–$C_8$ linear, branched or cyclic alkyl group; $R^5$ is independently selected from the group consisting of a $C_1$–$C_8$ linear, branched or cyclic alkyl group, a $C_1$–$C_8$ linear, branched or cyclic fluoroalkyl group, and combinations thereof; diene is a counter ligand independently selected from the group consisting of cyclooctadiene and norbornadiene; $A^-$ is an anion wherein A is independently selected from the group consisting of trifluoromethanesulfonate, tetrafluoroborate, hexafluoroantimonate, and hexafluorophosphate; $X^-$ is an anion wherein X is independently a halogen; and "*" designates an asymmetric carbon having (R)- or (S)-configuration.

2. A process for making enantiomerically enriched 4-piperidinylglycine having the formula (I),

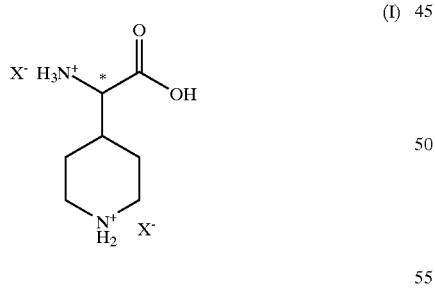

(I)

said process comprising (a) combining N-protected glycine ester having the formula (II)

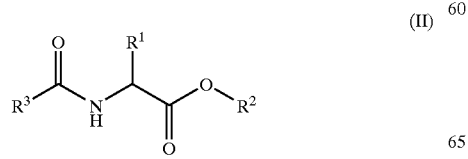

(II)

with 4-piperidone having the formula (III)

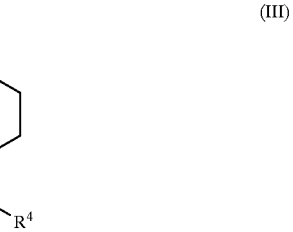

(III)

whereby didehydroamino acid ester is formed having the formula (IV);

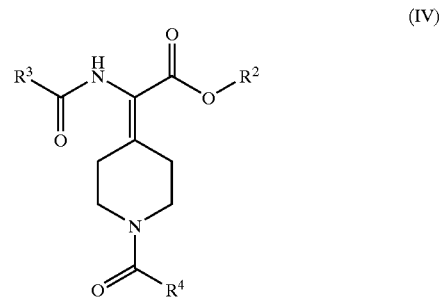

(IV)

(b) reducing the didehydroamino acid ester (IV) with hydrogen gas in the presence of a rhodium catalyst selected from the group consisting of (R,R)-BPE-Rh having the formula (A1), (S,S)-BPE-Rh having the formula (A2), (R,R)-DuPHOS-Rh having the formula (B1), (S,S)-DuPHOS-Rh having the formula (B2), and combinations thereof;

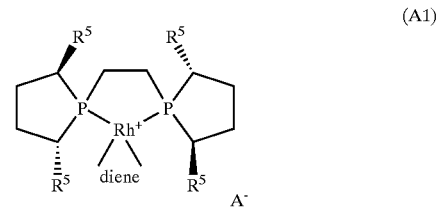

(A1)

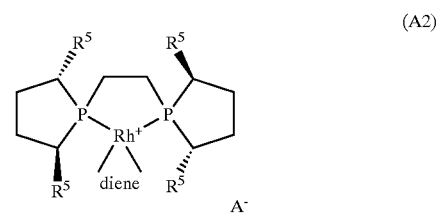

(A2)

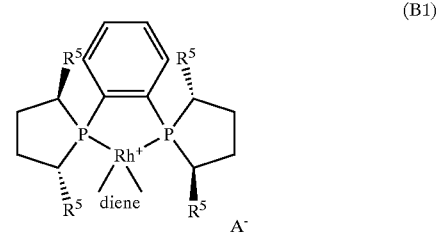

(B1)

(B2)

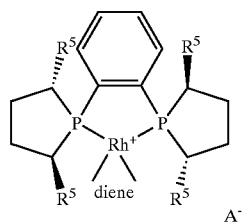

whereby a protected compound is formed having the formula (V);

(V)

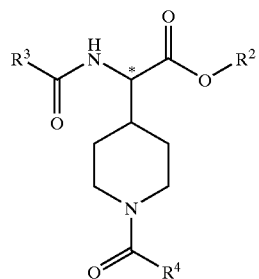

(c) removing the protecting group of formula (V), whereby a semi-protected compound is formed having the formula (VII)

(VII)

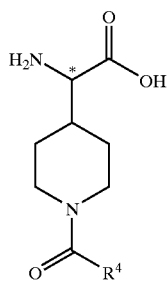

(d) removing the protecting group of formula (VII), whereby the 4-piperidinylglycine having the formula (I) is formed;
wherein $R^1$ is selected from the group consisting of hydrogen and $PO(OM)_2$, wherein M is a phenyl or $C_1$–$C_8$ linear, branched or cyclic alkyl group; $R^2$ is selected from the group consisting of hydrogen, phenyl and a $C_1$–$C_8$ linear, branched or cyclic alkyl group; $R^3$ and $R^4$ are independently selected from the group consisting of hydrogen, phenyl, a $C_1$–$C_8$ linear, branched or cyclic alkyl group, and $OR^6$, wherein $R^6$ is selected from the group consisting of hydrogen, phenyl, benzyl, substituted benzyl, and $C_1$–$C_8$ linear, branched or cyclic alkyl group; $R^5$ is independently selected from the group consisting of a $C_1$–$C_8$ linear, branched or cyclic alkyl group, a $C_1$–$C_8$ linear, branched or cyclic fluoroalkyl group, and combinations thereof; diene is a counter ligand independently selected from the group consisting of cyclooctadiene and norbornadiene; $A^-$ is an anion wherein A is independently selected from the group consisting of trifluoromethanesulfonate, tetrafluoroborate, hexafluoroantimonate, and hexafluorophosphate; $X^-$ is an anion wherein X is independently a halogen; and "*" designates an asymmetric carbon having (R)- or (S)-configuration.

3. The process according to claim 1 wherein the 4-piperidinylglycine is (R)4-piperidinylglycine.

4. The process according to claim 1 wherein the 4-piperidinylglycine is (S)4-piperidinylglycine.

5. The process according to claim 1 wherein $R^1$ is $PO(OCH_3)_2$; $R^2$ is $CH_3$; $R^3$ is $OCH_2Ph$, $R^4$ is $OC(CH_3)_3$; and $X^-$ is an anion wherein X is chlorine.

6. The process according to claim 1 wherein the rhodium catalyst is selected from the group consisting of [((R,R)-Me-BPE-Rh-(COD)]OTf; [((S,S)-Me-BPE-Rh-(COD)]OTf; [((R,R)-Me-DuPHOS-Rh-(COD)]OTf; and [((S,S)-Me-DuPHOS-Rh-(COD)]OTf having the respective formulas T1, T2, T3,T4, (T1)

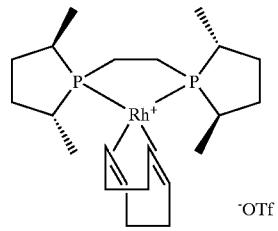

(T2)

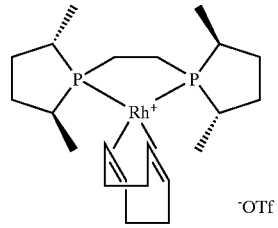

(T3)

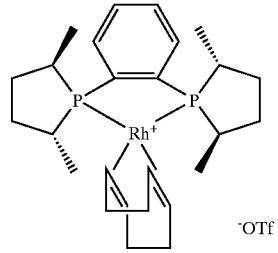

(T4)

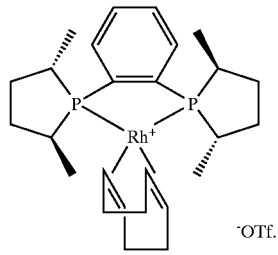

7. The process according to claim 1 wherein Step (b) is conducted at a temperature of from about 0° C. to about 60° C.

8. The process according to claim 7 wherein the temperature is from about 20° C. to about 28° C.

9. The process according to claim 1 wherein Step (b) is conducted under gaseous hydrogen pressure of from about 1 atm to about 200 atm.

10. The process according claim 9 wherein the pressure is from about 50 atm to about 100 atm.

11. The process according to claim 1 wherein Step (b) is conducted in the presence of at least one organic solvent.

12. The process according to claim 11 wherein the organic solvent is selected from the group consisting of methanol, ethanol, isopropanol, propanol, butanol, ethyl acetate, isopropyl acetate, chloroform, tert-butyl methyl ether, tetrahydrofuran, dimethoxyethane, dichloromethane, and combinations thereof.

13. The process according to claim 12 wherein the organic solvent is methanol.

14. A process according to claim 1, wherein the diene counter ligand is cyclooctadiene (COD) having formula D1 or norbornadiene (NBD) having formula D2

(D1)

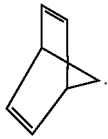
(D2)

15. The process according to claim 1 which additionally includes a separation step.

16. The process according to claim 15 wherein the separation step is selected from the group consisting of crystallization, chemical resolution, chiral preparative chromatography, and combinations thereof.

17. The process according to claim 16 wherein the separation step is crystallization.

* * * * *